United States Patent
Tokudome et al.

(12)

(10) Patent No.: US 6,721,595 B1
(45) Date of Patent: Apr. 13, 2004

(54) PERCUTANEOUS ABSORPTION PROMOTERS FOR ELECTROPORATION

(75) Inventors: Yoshihiro Tokudome, Yokohama (JP); Koji Owaku, Yokohama (JP); Kenichi Goto, Yokohama (JP); Kenji Sugibayashi, Kawagoe (JP)

(73) Assignee: Pola Chemical Industries Inc., Shizuoka (JP)

( * ) Notice: Subject to any disclaimer, the term of this patent is extended or adjusted under 35 U.S.C. 154(b) by 0 days.

(21) Appl. No.: 10/110,589

(22) PCT Filed: Apr. 6, 2000

(86) PCT No.: PCT/JP00/02244

§ 371 (c)(1),
(2), (4) Date: Apr. 11, 2002

(87) PCT Pub. No.: WO01/26688

PCT Pub. Date: Apr. 19, 2001

(30) Foreign Application Priority Data

Oct. 15, 1999 (JP) .............................. 11-293240

(51) Int. Cl.⁷ .............................. A61N 1/30; A61N 1/08; A61M 31/00; A61M 35/00; A61F 13/00

(52) U.S. Cl. .............................. 604/20; 604/289; 604/61; 424/448; 424/449; 607/39

(58) Field of Search .............................. 604/20, 289, 61; 424/448, 449; 607/152, 120, 39, 43, 20

(56) References Cited

U.S. PATENT DOCUMENTS

| 5,866,157 | A | * | 2/1999 | Higo et al. ............... 424/448 |
| 5,990,179 | A | | 11/1999 | Gyory et al. |
| 6,266,560 | B1 | * | 7/2001 | Zhang et al. ............... 604/20 |

FOREIGN PATENT DOCUMENTS

| JP | 9-255561 | 9/1967 |
| WO | WO 89/06555 | 7/1989 |

* cited by examiner

Primary Examiner—Brian L. Casler
Assistant Examiner—Roz Maiorino
(74) Attorney, Agent, or Firm—Knobbe, Martens, Olson & Bear, LLP

(57) ABSTRACT

The present invention relates to percutaneous sorbefacients for electroporation consisting of monoterpene and being useful in elevating percutaneous absorbability of drugs, etc. By adding these percutaneous sorbefacients to compositions for electroporation, the percutaneous absorbability of drugs can be elevated.

6 Claims, 1 Drawing Sheet

PERCUTANEOUS ABSORPTION PROMOTERS FOR ELECTROPORATION

CROSS-REFERENCE TO RELATED APPLICATIONS

This is the National Phase under 35 U.S.C. §371 of International Application No. PCT/JP00/02244, filed Apr. 6, 2000, which claims priority to Japanese Patent Application No. 11/293240 filed Oct. 15, 1999. The International Application was published under PCT Article 21(2) in a language other than English.

BACKGROUND OF THE INVENTION

1. Field of the Invention

The present invention relates to percutaneous sorbefacients for electroporation which are suitable for enhancing an efficiency of administrating drugs by electroporation and to compositions for electroporation comprising the same. The present invention is useful in the field of drugs.

2. Description of the Related Art

Although percutaneous absorption route has been expected as an administration route for drugs, since it gives less pain than injection does and also involves less possibility of forgetting to administrate drugs than oral administration does, it is considerably difficult to allow percutaneous absorption due to a preventive function that the skin inherently has. Under the present circumstances, however, the percutaneous absorption route has not been established yet as means for delivering drugs. As one devised method to overcome the present problem, a so-called electroporation may be exemplified according to which pores are formed in the skin structure by application of a voltage and a drug is delivered through these pores. Recently, it has become clearer that in such an electroporation, the behavior of drugs is different from that in ordinary administration so that it has been desired to develop compositions for percutaneous administration which are suitable for such an electroporation. Also, it has been desired to develop percutaneous sorbefacients having an effect of promoting percutaneous absorption of drugs under such an electroporation. Under the present circumstances, however, these have not been obtained yet.

Meanwhile, since monoterpenes such as menthol used as general-purpose materials in the field of skin external agents have not been used in electroporation, it has been unknown at all that they have excellent percutaneous sorbefacients effects in electroporation.

SUMMARY OF THE INVENTION

Under the aforementioned circumstances, the present invention has been made and is aimed at providing a percutaneous sorbefacients in electroporation and a composition for percutaneous administration which is suitable for electroporation comprising the same.

In consideration of such circumstances, the present inventors have made extensive studies with efforts in pursuit of a composition for electroporation having excellent percutaneous absorption effects. As a result, the inventors have found that monoterpenes such as menthol exhibit excellent percutaneous sorbefacient effects under electroporation and that incorporation of monoterpenes in compositions for electroporation can give rise to compositions for electroporation having excellent percutaneous sorbefacient effects, thereby achieving the present invention. That is, the present invention provides a percutaneous sorbefacient for electroporation consisting of monoterpene and compositions for electroporation comprising the same.

(1) Percutaneous sorbefacient for electroporation of the present invention

The percutaneous sorbefacient for electroporation of the present invention consisits of monoterpene. Preferred examples of the monoterpene include menthol and optical isomers thereof, menthone, thymol, geraniol, pinene, citral, citronellal, etc. Of those, menthol is preferred and 1-menthol is more preferred. This is because menthols in particular 1-menthol have excellent percutaneous sorbefacient effects in electroporation. There are some monoterpenes that exhibit percutaneous sorbefacient effects in ordinary percutaneous administration where no electric field is applied. In such a case, the percutaneous sorbefacient effect is only a few times larger than that of a case where no monoterpene exists. In contrast, the percutaneous sorbefacient effect of the monoterpenes under electroporation according to the present invention is from several tens to several hundreds of times larger than that of a case where neither electric field is applied to nor monoterpene is added. Thus, there is exhibited a percutaneous sorbefacient effect enhanced to such an extent as is by no means expectable from the conventionally known percutaneous sorbefacient effect. In the compositions for electroporation of the present invention, a preferred content of the monoterpenes, which are percutaneous sorbefacients of the present invention is 0.1 to 10% by weight, more preferably 0.5 to 5% by weight. This is because if the monoterpenes are too much, they cause irritation in some cases and if they are too little, no percutaneous sorbefacient effect can be obtained in some cases.

(2) Compositions for electroporation of the present invention

The composition for electroporation of the present invention comprises the aforementioned percutaneous sorbefacient for electroporation. The compositions for electroporation of the present invention may comprise besides the monoterpenes (the percutaneous sorbefacients of the present invention), which are essential components, optional components for manufacturing pharmaceutical preparations used in ordinary composition for electroporation. Preferred examples of such optional components include hydrocarbons such as squalene, vaseline, microcrystalline wax, esters such as jojoba oil, carnauba wax, and octyldodecyl oleic acid, triglycerides such as olive oil, beef tallow, and coconut oil, fatty acids such as stearic acid, oleic acid and ricinoleic acid, higher alcohols such as oleyl alcohol, stearyl alcohol, and octyldodecanol, anionic surfactants such as sulfosuccinic acid esters and sodium polyoxyethylenealkylsulfates, amphoteric surfactants such as alkylbetaine salts, cationic surfactants such as dialkylammonium salts, nonionic surfactants such as sorbitan fatty acid esters, fatty acid monoglycerides, polyoxyethylene adducts of these, polyoxyethylene alkyl ethers and polyoxyethylene fatty acid esters, viscosity bodying and gelling agents, antioxidants, ultraviolet absorbents, coloring agents, preservatives, powders and the like. Further, as drugs that are percutaneously administered by such an electroporation, those usually used as medical preparations can be applied without any particular limitation. Preferred examples of such drags include analgesic antipyretic anti-inflammatory agents such as codeine, morphine, hydromorphone, oxycodone, pethidine, buprenorphin hydrochloride, pentazocine, and tramadol hydrochloride, protein-based drugs such as insulin, carcitonine, elcatonin, adrenocorticotrophic hormone (ACTH), parathyroid hormone (PTH), selectin, oxytocin, angiotensin, β-endorphin, vasopressin, glucagon, somatostatin, luteinizing hormone-releasing hormone (LH-RH), enkephalin, neurotensin, atrial sodium diuretic peptide (ANP), growth hormone, bradykinin, substance P, dynorphin, thyroid stimulating hormone (TSH), prolactin, G-CSF, glutathione peroxidase, super-oxide dismutase (SOD), desmopressin, somatomedin, melanocyte stimulating hormone (MSH), calcitonin gene related peptide (CGRP), endothelin, and thyrotropin releasing hormone (TRH), interleukins, interferons, anti-platelet drugs, vasodilaters, argatroban as anti-arteriosclerotic drug, salpogrelate hydrochloride, sodium beraprost, limaprost alfadex, and cilostazol and the like. These drugs should be administered with passage of time by necessary amounts so that they are agreeable to the properties of percutaneous administration. The compositions for electroporation of the present invention are processed into preparations forms in conformity with the physical properties of the active ingredients, such as solutions, emulsions, semi-solids, and solids, by treating the aforementioned essential components, preferred components, optional components and active ingredients, and are used in electroporation. That is, by using the compositions of the present invention, drugs as active ingredients can be percutaneously administered by electroporation. Upon electroporation, they are used together with a device for electroporation. Among the aforementioned preparation forms, preferred one includes aqueous preparation forms and particularly preferred are an aqueous solution preparation form, aqueous gel preparation form and emulsion preparation form.

(3) Unit for administrating a drug for external application to the skin

The unit for administrating drugs for external application to the skin of the present invention includes the composition for electroporation and a device for electroporation of the present invention in combination. The device for electroporation is not particularly limited as far as it is used usually in such a use, and for example, those devices described in Japanese Domestic Patent Laid Open Publication No. Hei 11-507341(laying open of a Japanese translation), Japanese Domestic Patent Laid open Publication No. Hei 11-505445 (laying open of a Japanese translation), Japanese Domestic Patent Laid Open Publication No. Hei 10-502827(laying open of a Japanese translation), Japanese Domestic Patent Laid Open Publication No. Hei 11-503349(laying open of a Japanese translation), Japanese Domestic Patent Laid Open Publication No. Hei 08-511680(laying open of a Japanese translation), Japanese Domestic Patent Laid Open Publication No. Hei 03-502416(laying open of a Japanese translation), etc. may be used. Further, those commercially available devices for such an electroporation include ECM-600 produced by BTX Co., GENE PULSER produced by BIO-RAD Co., etc. Also, these may be used. As for the conditions of electroporation, it is preferred to impress electric current for about 30 seconds with the voltage set to about 300 V and the capacitance of capacitor set to about 25 RF.

BEST MODE FOR CARRYING OUT THE INVENTION

Figure 1:
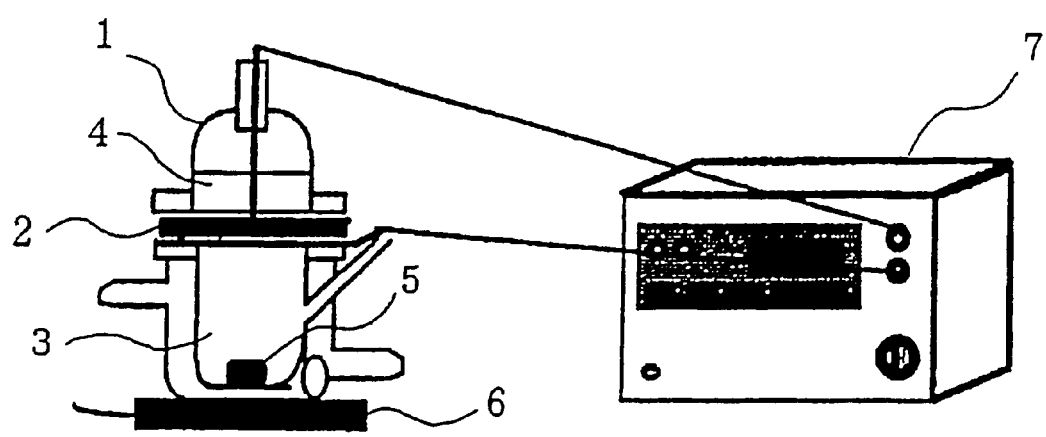
FIG. 1 is a diagram showing the apparatus for electroporation used in Example 1.

Hereinafter, the present invention will be described in more detail by way of providing examples. Of course, the present invention is not limited to the examples.

EXAMPLE 1

According to the recipe shown in Table 1, compositions for electroporation of the present invention were prepared.

As a model labeled drug, 1 mM sodium calcein was used. These were stirred and solubilized to prepare a composition (liquid agent) for electroporation of the present invention. This was measured for its percutaneous sorbefacient effect by a percutaneous permeability test by using a Franz cell. More particularly, to a Franz cell 1, a skin sample 2 which had been obtained from the abdominal part of a hairless rat and from which subcutaneous fat had been removed was attached as a separator with the keratin layer directed toward the donor side. The receiver side was filled with physiological saline 3 while the donor side was filled with 3 ml of the composition 4 for electroporation of the present invention. The receiver side was stirred at 1,200 rpm by a stirrer 6 by use of a star-head type stirrer 5. Each 0.3 ml aliquot was collected with passage of time and the same amount of physiological saline was added and percutaneous permeability was examined. The amount of sodium calcein was measured by using a fluorometer. As the control, 1 mM sodium calcein physiological saline solution was used. The electroporation was conducted under the conditions of using GENE PULSER produced by BIO-RAD Co. as a pulse voltage generator 7 at 300 V with a capacitance of a capacitor of 25 $\mu$F with applying 1 pulse (0.5 minute intervals) in first 5 minutes out of 60 minutes and turning off the voltage for the remaining 55 minutes. The results are shown in Table 1 in terms of cumulative permeation amount for 6 hours (nmol/cm$^2$). From this, it is evident that the composition for electroporation of the present invention has excellent percutaneous sorbefacient effect. Comparing this with a case without any electroporation, such an effect is a synergistic effect due to combined use with electroporation (EP) Further, it can be seen that the effect obtained by addition of monoterpene is superior to any of the percutaneous sorbefacient effects of various percutaneous sorbefacients in ordinary cases where no electric field is applied. This apparatus is shown in FIG. 1.

TABLE 1

| Composition | Comparative Example | Example 1 |
| --- | --- | --- |
| Physiological saline sodium calcein | 50 parts by weight (1 mM; final concentration) | 47 parts by weight (1 mM; final concentration) |
| Propylene glycol | 50 parts by weight | 50 parts by weight |
| 1-Menthol | | 3 parts by weight |
| Six hour cumulative percutaneous permeation Under electric field Under no electric field | 0.47 245.04 | 28.34 800.85 |

EXAMPLE 2

According to the recipe shown below, a composition for electroporation of the present invention was prepared. That is, the components in the recipe were stirred and solubilized to prepare a composition for electroporation.

| | |
| --- | --- |
| Physiological saline | 69 parts by weight |
| Buprenorphin hydrochloride | 1 part by weight |
| Propylene glycol | 28 parts by weight |
| 1-Menthol | 2 parts by weight |

EXAMPLE 3

According to the recipe shown below, a composition for electroporation of the present invention was prepared. That is, the components in the recipe were stirred and solubilized to prepare a composition for electroporation.

| Physiological saline | 69 parts by weight |
|---|---|
| Buprenorphin hydrochloride | 1 part by weight |
| Propylene glycol | 28 parts by weight |
| Geraniol | 2 parts by weight |

EXAMPLE 4

According to the recipe shown below, a composition for electroporation of the present invention was prepared. That is, the components in the recipe were stirred and solubilized to prepare a composition for electroporation.

| Physiological saline | 69 parts by weight |
|---|---|
| Buprenorphin hydrochloride | 1 part by weight |
| Propylene glycol | 28 parts by weight |
| Citral | 2 parts by weight |

EXAMPLE 5

According to the recipe shown below, a composition for electroporation of the present invention was prepared. That is, the components in the recipe were stirred and solubilized to prepare a composition for electroporation.

| Physiological saline | 69 parts by weight |
|---|---|
| Buprenorphin hydrochloride | 1 part by weight |
| Glycerin | 28 parts by weight |
| 1-Menthol | 2 parts by weight |

EXAMPLE 6

According to the recipe shown below, a composition for electroporation of the present invention was prepared. That is, the components in the recipe were stirred and solubilized to prepare a composition for electroporation.

| Physiological saline | 69 parts by weight |
|---|---|
| Buprenorphin hydrochloride | 1 part by weight |
| Dipropylene glycol | 28 parts by weight |
| 1-Menthol | 2 parts by weight |

EXAMPLE 7

According to the recipe shown below, a composition for electroporation of the present invention was prepared. That is, the components in the recipe were stirred and solubilized to prepare a composition for electroporation.

| Physiological saline | 69 parts by weight |
|---|---|
| Insulin | 1 part by weight |
| Propylene glycol | 28 parts by weight |
| 1-Menthol | 2 parts by weight |

EXAMPLE 8

According to the recipe shown below, a composition for electroporation of the present invention was prepared. That is, the recipe component A was stirred, dispersed and solubilized and the recipe component B was added thereto to neutralize the mixture and obtain a composition (gel) for electroporation.

| Physiological saline | 48 parts by weight |
|---|---|
| Carboxyvinyl polymer | 0.6 part by weight |
| Buprenorphin hydrochloride | 1 part by weight |
| Propylene glycol | 30 parts by weight |
| 1-Menthol | 1 part by weight |
| Physiological saline | 19 parts by weight |
| Potassium hydroxide | 0.4 part by weight |

INDUSTRIAL APPLICABILITY

According to the present invention, a percutaneous sorbefacient in electroporation and a composition for percutaneous administration which is suitable for electroporation can be provided and the present invention is useful in the field of drugs.

What is claimed is:

1. A unit for administrating a drug for external application to skin, comprising a composition for administrating the drug by electroporation, which consists essentially of the drug and a percutaneous sorbefacient consisting of one or more monoterpenes and a device for electroporation in combination, wherein a content of the percutaneous sorbefacient is 0.1 to 5% by weight and wherein the absorption of the drug is from several tens to several hundreds of times larger than absorption of the drug in the absence of the one or more monoterpenes and electroporation.

2. The unit for administrating a drug for external application to skin according to claim 1, wherein the monoterpene is menthol.

3. A method for administrating a drug to a patient by electroporation, comprising the steps of:

applying a composition essentially of the drug and one or more monoterpenes to skin; and impressing electric current to the skin, thereby elevating a percutaneous absorbability of the drug to the skin and permeating the drug through the skin, wherein a content of the one or more monoterpenes is 0.1 to 5% by weight and wherein the absorption of the drug is from several tens to several hundreds of times larger than absorption of the drug in the absence of the one or more monoterpenes and electroporation.

4. The method for administrating the drug according to claim 3, wherein the monoterpene is menthol.

5. The method for administrating the drug according to claim 3, wherein the monoterpene is one or more selected from the group consisting of menthol and optical isomers thereof, menthone, thymol, geraniol, pinene, citral and citronellal.

6. The unit for administrating the drug for external application to skin according to claim 1, wherein the one or more monoterpenes are selected from the group consisting of menthol and optical isomers thereof, menthone, thymol, geraniol, pinene, citral and citronellal.

* * * * *

UNITED STATES PATENT AND TRADEMARK OFFICE
CERTIFICATE OF CORRECTION

PATENT NO. : 6,721,595 B1
DATED : April 13, 2004
INVENTOR(S) : Tokudome et al.

It is certified that error appears in the above-identified patent and that said Letters Patent is hereby corrected as shown below:

Column 6,
Line 41, "a composition essentially of the drug" should be changed to -- a composition consisting essentially of the drug --

Signed and Sealed this

Twentieth Day of July, 2004

JON W. DUDAS
*Acting Director of the United States Patent and Trademark Office*

(12) EX PARTE REEXAMINATION CERTIFICATE (5577th)
United States Patent
Tokudome et al.

(10) Number: US 6,721,595 C1
(45) Certificate Issued: Oct. 17, 2006

(54) PERCUTANEOUS ABSORPTION PROMOTERS FOR ELECTROPORATION

(75) Inventors: Yoshihiro Tokudome, Yokohama (JP); Koji Owaku, Yokohama (JP); Kenichi Goto, Yokohama (JP); Kenji Sugibayashi, Kawagoe (JP)

(73) Assignee: Pola Chemical Industries, Inc., Shizuoka (JP)

Reexamination Request:
No. 90/007,465, Mar. 14, 2005

Reexamination Certificate for:
Patent No.: 6,721,595
Issued: Apr. 13, 2004
Appl. No.: 10/110,589
Filed: Apr. 11, 2002

Certificate of Correction issued Jul. 20, 2004.

(22) PCT Filed: Apr. 6, 2000
(86) PCT No.: PCT/JP00/02244
§ 371 (c)(1),
(2), (4) Date: Apr. 11, 2002
(87) PCT Pub. No.: WO01/26688
PCT Pub. Date: Apr. 19, 2001

(30) Foreign Application Priority Data
Oct. 15, 1999 (JP) ............................................ 11-293240

(51) Int. Cl.
*A61N 1/30* (2006.01)
*A61N 1/08* (2006.01)
*A61M 31/00* (2006.01)
*A61M 35/00* (2006.01)
*A61F 13/00* (2006.01)

(52) U.S. Cl. ........................... 604/20; 604/61; 604/289; 424/448; 424/449; 607/39

(58) Field of Classification Search ................. None
See application file for complete search history.

(56) References Cited

U.S. PATENT DOCUMENTS

| | | | |
|---|---|---|---|
| 4,933,184 A | * 6/1990 | Tsuk | ........................... 424/449 |
| 5,019,034 A | 5/1991 | Weaver et al. | |
| 5,069,908 A | 12/1991 | Henley | |
| 6,302,874 B1 | * 10/2001 | Zhang et al. | ................ 604/522 |
| 6,527,759 B1 | 3/2003 | Tachibana et al. | |
| 6,532,386 B1 | * 3/2003 | Sun et al. | ....................... 604/20 |
| 6,678,558 B1 | 1/2004 | Dimmer et al. | |
| 6,697,669 B1 | * 2/2004 | Dev et al. | ..................... 604/21 |
| 6,743,432 B1 | 6/2004 | Yanai et al. | |

FOREIGN PATENT DOCUMENTS

| | | |
|---|---|---|
| DE | 39 25 680 A1 | 2/1991 |
| EP | 0 480 054 A1 | 10/1991 |
| GB | 2 239 600 | 7/1991 |
| GB | 2 239 600 A | 7/1991 |
| JP | 06016538 | 1/1994 |
| WO | WO 96/00111 | 1/1996 |
| WO | WO 00/23099 | 4/2000 |

OTHER PUBLICATIONS

Sun, Skin Absorption Enhancement by Physical Means: Heat, Ultrasound, and Electricity, Transdermal and Topical Drug Delivery Systems,1997, Interpharm Press, pp. 327–55.*
Supplementary European Search Report completed Feb. 3, 2005 and issued to related foreign application.
Supplementary European Search Report dated Jan. 18, 2005 as issued to a related foreign application.
Supplementary European Search Report dated Marcy 24, 2004 as issued to related foreign application.

* cited by examiner

*Primary Examiner*—Michael O'Neill

(57) ABSTRACT

The present invention relates to percutaneous sorbefacients for electroporation consisting of monoterpene and being useful in elevating percutaneous absorbability of drugs, etc. By adding these percutaneous sorbefacients to compositions for electroporation, the percutaneous absorbability of drugs can be elevated.

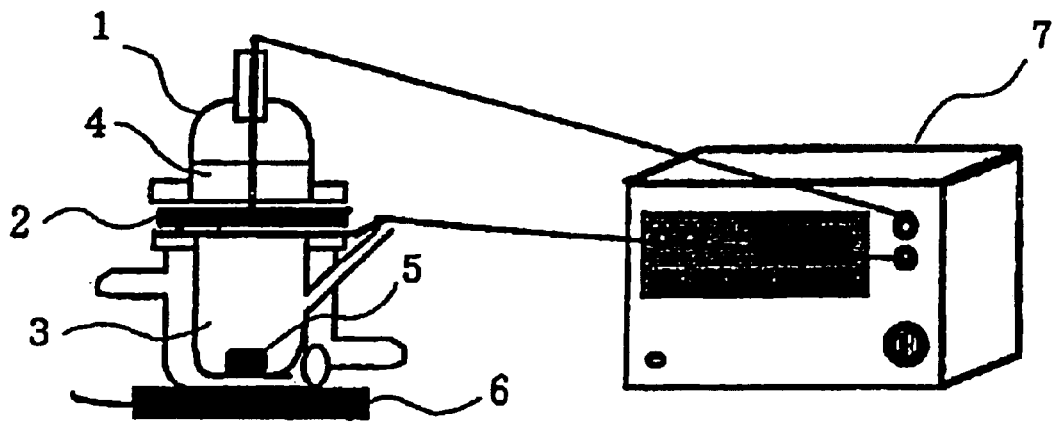

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 3 are determined to be patentable as amended.

Claims 2 and 4–6, dependent on an amended claim, are determined to be patentable.

1. A unit for administrating a drug for external application to skin, [comprising] *consisting of* a composition for administrating the drug by electroporation, which consists essentially of the drug and a percutaneous sorbefacient consisting of one or more monoterpenes and a device for electroporation in combination, wherein a content of the percutaneous sorbefacient to 0.1 to 5% by weight and wherein the absorption of the drug is from several tens to several hundreds of times larger than absorption of the drug in the absence of the one or more monoterpenes and electroporation.

3. A method for administrating a drug to a patient by electroporation, [comprising] *consisting of* the steps of:
applying a composition consisting essentially of the drug and one or more monoterpenes to skin; and
impressing electric current to the skin, thereby elevating a percutaneous absorbability of the drug to the skin and permeating the drug through the skin, wherein a content of the one or more monoterpenes is 0.1 to 5% by weight and wherein the absorption of the drug is from several tens to several hundreds of times larger than absorption of the drug in the absence of the one or more monoterpenes and electroporation.

* * * * *